United States Patent [19]

Matzuk

[11] 4,398,425
[45] Aug. 16, 1983

[54] ULTRASONIC SCANNING TRANSDUCER

[75] Inventor: Terrance Matzuk, Pittsburgh, Pa.

[73] Assignee: Dymax Corporation, Pittsburgh, Pa.

[21] Appl. No.: 289,312

[22] Filed: Aug. 3, 1981

[51] Int. Cl.³ .............................................. G01N 29/04
[52] U.S. Cl. ........................................ 73/633; 73/634; 73/639
[58] Field of Search .................. 73/633, 634, 639, 641

[56] References Cited

U.S. PATENT DOCUMENTS

| | | | |
|---|---|---|---|
| 4,092,867 | 6/1978 | Matzuk | 73/642 |
| 4,102,204 | 7/1978 | Kretz | 73/639 |
| 4,228,687 | 10/1980 | Fraser | 73/641 |
| 4,269,066 | 5/1981 | Fischer | 73/639 |

*Primary Examiner*—Anthony V. Ciarlante
*Attorney, Agent, or Firm*—Robert D. Yeager; Andrew J. Cornelius

[57] ABSTRACT

The present invention provides an ultrasonic scanning transducer for use in an ultrasonic scanning system that examines an object by directing a series of ultrasonic waves into the object, receiving electrical signals related to the echoes generated by the ultrasonic waves when they strike acoustical interfaces within the object, and displaying the information borne by the electrical signals relating to the nature and location of acoustical interfaces within the object. The ultrasonic scanning transducer includes transducer elements secured to a permanent magnet mounted for rotational movement within the housing of the transducer and a stator assembly for rotating the transducers and magnet continuously in a single direction. The stator assembly receives a periodic signal having a zero average value and creates therefrom a unidirectionally rotating magnetic field which exerts a force on and rotates the permanent magnet.

31 Claims, 12 Drawing Figures

ULTRASONIC SCANNING TRANSDUCER

BACKGROUND OF THE INVENTION

1. Field of the Invention

The present invention relates to ultrasonic scanning systems and, in particular, to an ultrasonic scanning transducer for examining an object.

2. Description of the Prior Art

Ultrasonic scanning systems are being used presently to examine objects of various natures to determine their characteristics. Physicians and medical technicians are using ultrasonic scanning systems to detect abnormalities in the human body and to examine human fetuses in the mothers' uteri. Further, ultrasonic scanning systems are being used to discover the existence and location of inanimate objects and materials and to inspect metals and metal objects for flaws.

Basically, the ultrasonic scanning transducer of an ultrasonic scanning system gather data relating to the nature of the object by directing a series of ultrasonic waves into an object and receiving and processing the series of echoes generated when the waves strike acoustical interfaces within the object. Examples of an acoustical interface include the interface between the human organ and the tissue surrounding the organ and the interface between a piece of metal and a flaw located within it. Generally, the echoes generated at the acoustical interfaces are converted to electrical signals by the transducer. Those signals are processed and transmitted to the scanning system for further processing and display, commonly on a cathode-ray tube. By properly timing the generation of ultrasonic waves and the processing of returning echoes, the transducer can produce electrical signals containing information relating to the existence of acoustical interfaces in the object and the nature of the material surrounding those interfaces. By properly scanning the object and displaying on the cathode-ray tube the electrical signals produced by the transducer, the examiner can actually see an image of a portion of the object under examination, including acoustical interfaces located within it. An example of such an ultrasonic scanning system and transducer therefor can be found in U.S. Pat. No. 4,092,867 issued to the applicant herein.

Several factors determine the level of desirability of an ultrasonic transducer. The first factor is the resolution of the scanning system. If the resolution is not adequate, the image displayed on the cathode-ray tube will not accurately depict the object. The second factor is the number of gray levels available with the display. The usefullness of the displayed image increases with the number of gray levels with which the displayed image is constructed. The third factor is the ease with which the system can be used. The size, shape and weight of the transducer itself determine in part the ease with which the entire scanning system can be used. The fourth factor is the cost of the transducer.

SUMMARY OF THE INVENTION

The present invention provides an image with good resolution and a satisfactory number of gray levels, is easy to manipulate and use, and can be produced for a relatively low cost.

The ultrasonic scanning transducer of the present invention is adapted for use in an ultrasonic scanning system that examines an object by directing a timed series of ultrasonic waves into the object and extracting information from the ultrasonic echoes created by the ultrasonic waves striking acoustical interfaces within the object. The ultrasonic scanning transducer can be used in any suitable existing scanning system such as that disclosed in U.S. Pat. No. 4,092,867 issued to the applicant herein.

The present invention includes a housing containing matter through which ultrasonic waves and echoes can travel. Apparatus, such as an ultrasonic transducer element, is disposed within the housing for creating ultrasonic waves from electrical energy and for creating information—carrying electrical energy from ultrasonic echoes returning from the object. A permanent magnet is disposed within the housing and mounted for rotational movement for supporting at least one of the ultrasonic wave creating and electrical energy creating apparatus. Bearing apparatus is provided for mounting the permanent magnet for rotational movement. Apparatus is also included within the housing for receiving a periodic electrical signal having a zero average value and creating therefrom a unidirectionally rotating primary magnetic field capable of exerting a force on the permanent magnet and thereby rotating the permanent magnet in the direction of rotation of the primary magnetic field. Accordingly, as the permanent magnet is rotated, the ultrasonic wave or electrical energy creating apparatus is rotated in one direction and in one plane within the housing.

Accordingly, the permanent magnet and the electrical energy creating apparatus constitute a single or multiphase motor driven by a periodic electrical signal with a zero average value. Preferably, the electrical energy creating apparatus is a stator assembly that is secured in the housing within an opening in the permanent magnet. The stator assembly includes windings which, when energized, create a unidirectionally rotating magnetic field that causes the permanent magnet to rotate around the stator assembly.

The present invention can also include timing circuits for synchronizing ultrasonic wave creation, ultrasonic echo reception and system image generation.

Further, the present invention can include circuits for creating the periodic electrical signal that establishes the magnetic field and rotates the permanent magnet.

Accordingly, the present invention is useful for examining an object and providing, in real-time, information useful for determing the nature of the object.

When used in this application, the terms "transducer element" or "ultrasonic transducer element" shall mean any device that produces an ultrasonic wave in response to receipt of energy in electrical form.

BRIEF DESCRIPTION OF THE DRAWINGS

The following detailed description of the preferred embodiments can be understood better by referring to the accompanying drawings, in which.

DETAILED DESCRIPTION OF THE PREFERRED EMBODIMENTS

Figure 1:
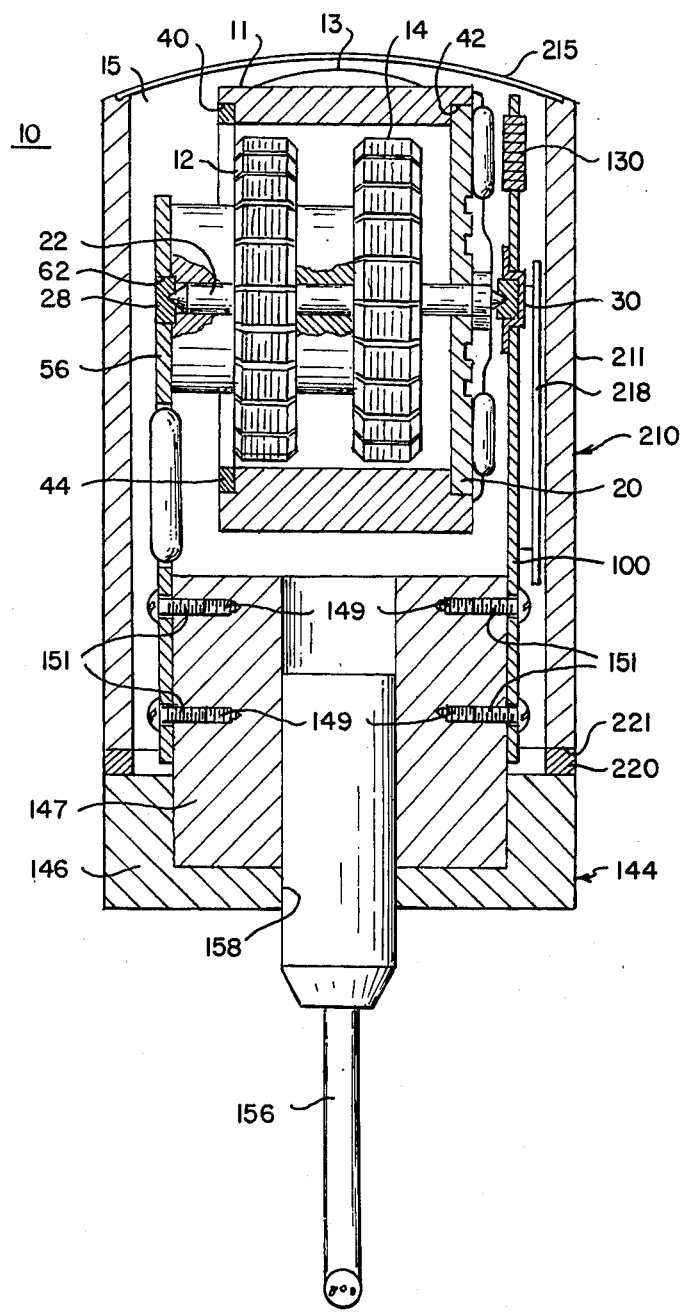
FIG. 1 is a side view, partly in section, of an ultrasonic scanning transducer constructed according to the provisions of the present invention.
Figure 2:
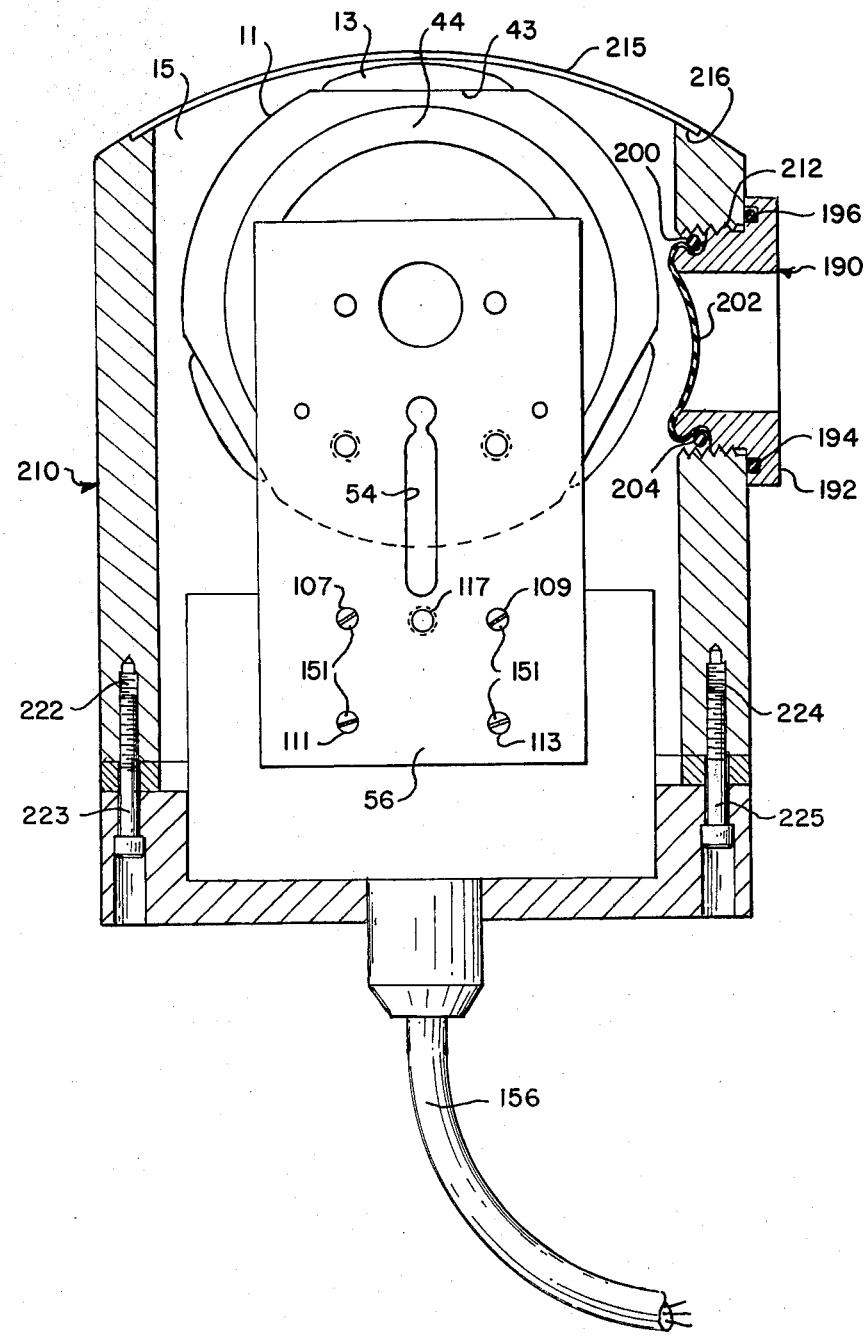
FIG. 2 is a side view, partly in section, of the ultrasonic scanning transducer shown in FIG. 1.
Figure 3:
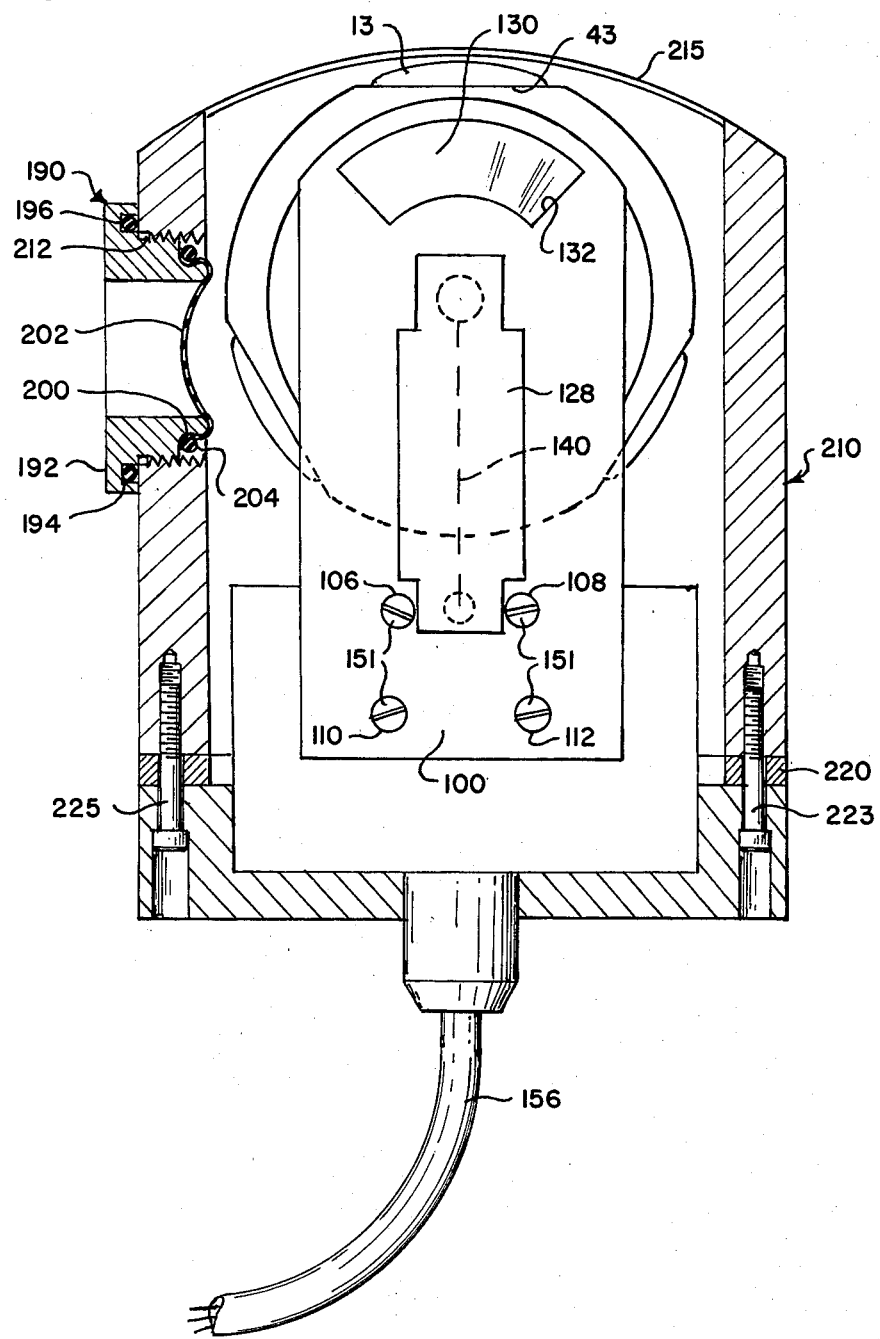
FIG. 3 is a side view, partly in section, of the ultrasonic scanning transducer shown in FIG. 1.
Figure 4:
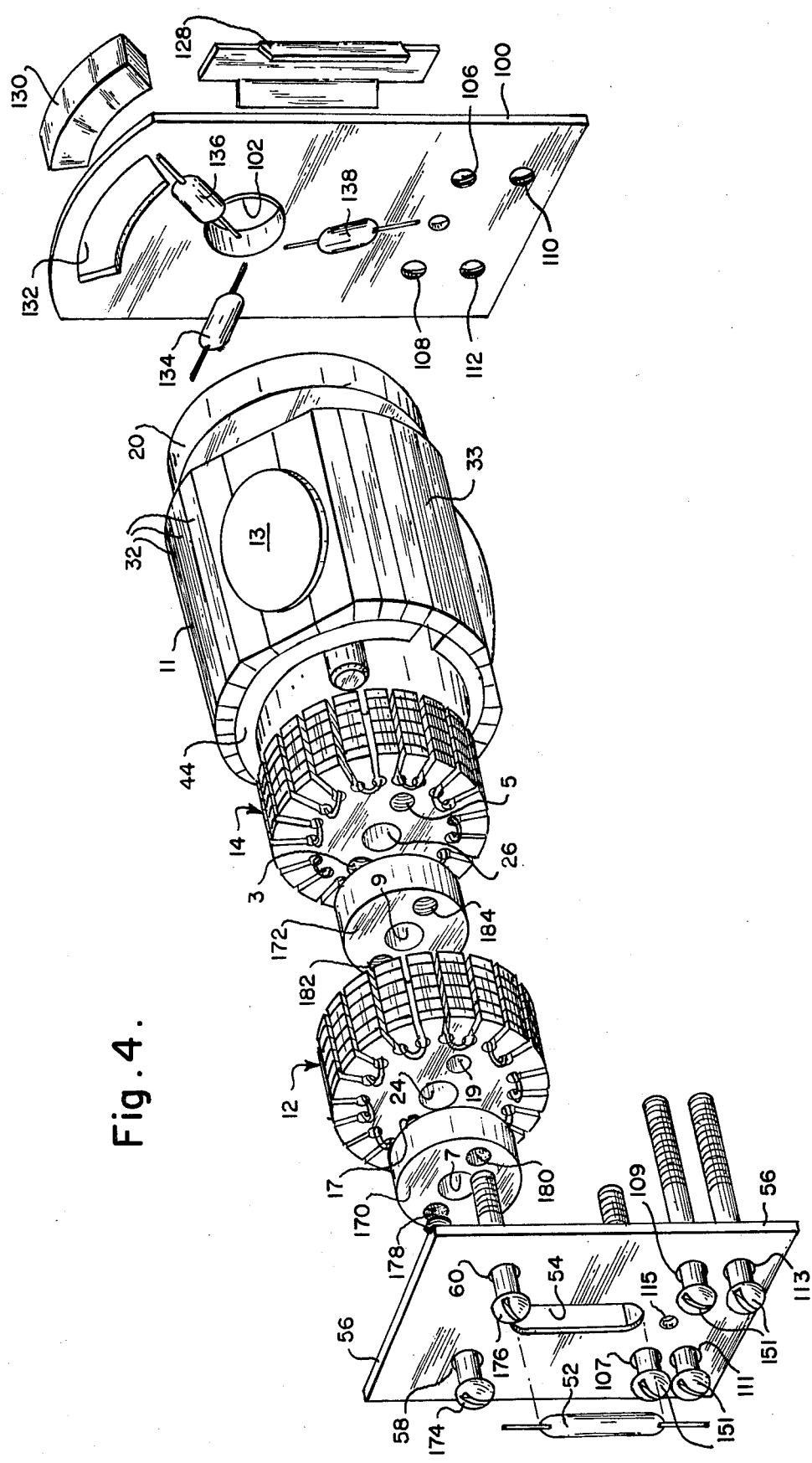
FIG. 4 is an exploded isometric view showing the stator assembly, the permanent magnet assembly and the support apparatus therefor for the ultrasonic scanning transducer shown in FIG. 1.

FIGS. 1 through 8 show the components constituting the preferred embodiment 10 of the present invention. The components of transducer 10 constitute a two-phase synchronous motor operated as a stepping motor during the start-up period of transducer 10.

Ultrasonic transducer 10 includes a permanent magnet assembly 11 which is mounted for rotation around two stator assemblies 12 and 14. A periodic signal having a zero average value is applied to coils 16 and 18 of stators 12 and 14, respectively. The periodic signal causes coils 16 and 18 to establish a unidirectionally rotating magnetic field that exerts a torque on magnet assembly 11 causing magnet assembly 11 to rotate about stator assemblies 12 and 14. Accordingly, stator assemblies 12 and 14 and permanent magnet 11 function together like a rotating synchronous motor. Transducer elements 13 are secured to the periphery of magnet assembly 11 and rotate therewith within housing 210. A transducer element 13 is made operative by transducer 10 only if it is in a position to direct ultrasonic waves and receive echoes through spherical plate 215.

Figure 6:
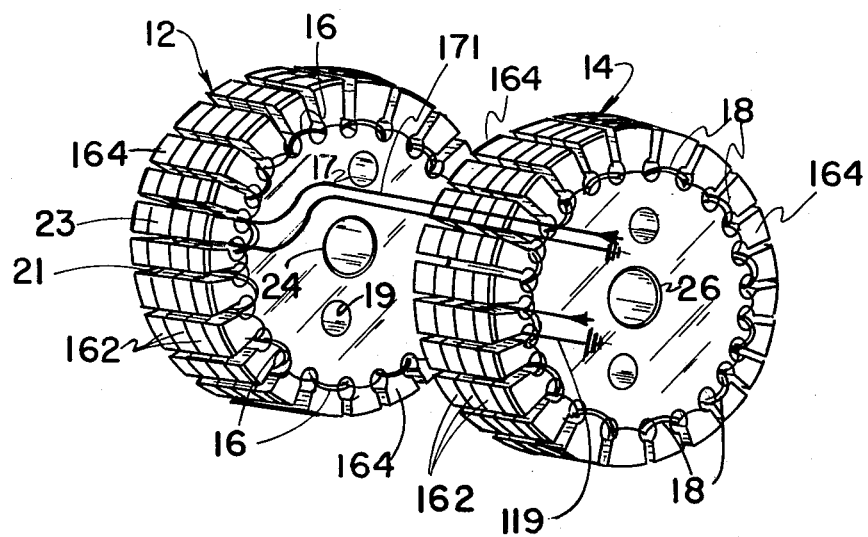
FIG. 6 is an isometric view of the stator assemblies shown in FIG. 4 that illustrates the winding pattern for the coils of the stator assemblies.

Preferably, coils 16 and 18 are wound on stators 12 and 14 as shown in FIG. 6 to provide an angular separation between coils 16 and 18 of 90 electrical degrees. Such a separation is desirable to ensure that transducer 10 can be started without regard to the initial position of magnet assembly 11 relative to stator assemblies 12 and 14. Each set of twelve coils 16 and 18 is formed by a single electrical conductor 171 or 191. Each coil 16 or 18 is formed with twenty-eight turns of conductor 171 or 191 disposed within a pair of slots 21 and wrapped around a core 23. FIG. 6 shows the layers that constitute each stator assembly 12 and 14. Layers 164 constitute the two ends of each stator assembly 12 and 14 and are constructed from fibroid fish paper. Four layers 162 form the core of each stator assembly 12 and 14 and are constructed from cold rolled steel. It should be noted that transducer 10 can be adapted to operate from a three-phase energizing signal simply by adding a third stator assembly having twelve coils formed thereon; however, each coil should be shifted from each other by 60 or 120 electrical degrees, depending upon the polarity of the energizing currents from the three-phase energizing signal.

Figure 5:
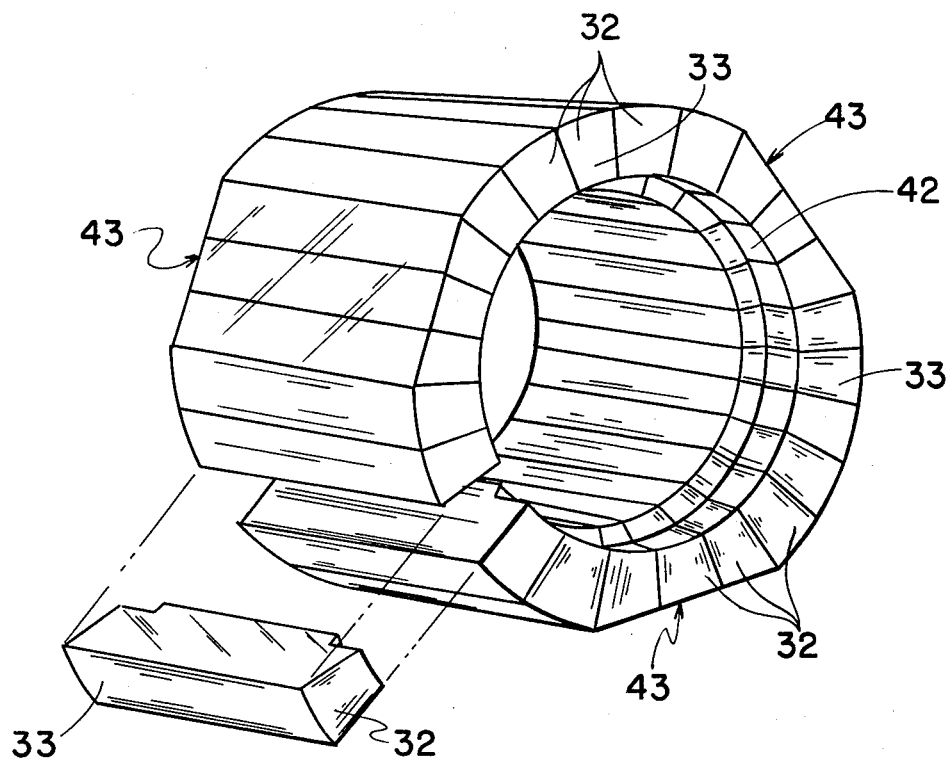
FIG. 5 is an exploded isometric view showing the permanent magnet assembly of the ultrasonic scanning transducer shown in FIG. 1.

As can be seen best in FIG. 5, magnet assembly 11 is formed from twenty-four individual wedge-shaped magnet elements 32. Elements 32 are cut from a suitable magnetic material and joined together to provide twenty-four magnet elements 32 each having a polarity opposite to that of each element 32 adjacent to it. If a third stator assembly having twelve coils is desired, magnet assembly 11 should be formed from thirty-six magnet elements 32. Magnet assembly 11 has two shoulders 40 and 42 for receiving ring 44 and plate 20, respectively. After magnet assembly 11 is formed, three flat surfaces 43 are machined in the periphery of magnet assembly 11 to provide seats for the three transducer elements 13. Transducer elements 13 are secured to seats 43 in any suitable fashion.

Shaft 22 supports magnet assembly 11 and stator assemblies 12 and 14. Shaft 22 passes through openings 24 and 26 of stator assemblies 12 and 14, respectively. Shaft 22 is supported at its ends by plate 100 through contact block 30 and plate 56 through contact 28 and, accordingly, can rotate about its longitudinal axis. Contact block 30 and contact 28 prevent shaft 22 from moving in its axial direction. Plates 100 and 56 are constructed of a material capable of conducting electrical current and that is mechanically resilient. Plates 100 and 56 are mounted to exert compressive force on the ends of shaft 22 to ensure it remains disposed therebetween, even after contact 28 and contact 116 of block 30 become worn. Plate 100 is thinner than plate 56 and, accordingly, moves toward shaft 22 as contact 116 becomes worn. Plate 56 also moves toward shaft 22 as contact 28 becomes worn, but its movement is much less than that of plate 100. Plate 20 is secured at its periphery to shoulder 42 of magnet assembly 11. Openings 24 and 26 of stator assemblies 12 and 14 provide bearings for preventing radial and processional movement of shaft 22. A brass ring 44 is secured to shoulder 40 of magnet assembly 11. Plate 20 and ring 44 prevent the shape of the ends of magnet assembly 11 from becoming distorted when magnet assembly 11 absorbs a portion of the acoustically-transparent liquid 15 disposed within housing 210.

As described above, a carbon contact 28 is mounted in opening 62 of plate 56 to provide the mounting for one end of shaft 22 and to provide electrical communication between plate 56 and shaft 22. Plate 100 includes an opening 102 for receiving a carbon contact block 30. Carbon contact 116 of contact block 30 receives nipple 98 of cap 96 which is soldered to end plate 20. Plate 100 is mounted to exert a compressive force on plate 20. Accordingly, contact 116 provides support for the remaining end of shaft 22 and provides electrical communication between region 88 of plate 20 and cable 156. Spacers 170 and 172 separate stator assemblies 12 and 14; openings 7 and 9 of spacers 170 and 172, respectively, provide bearings which prevent radial and precessional movement of shaft 22. Bolts 174 and 176 pass through openings 58 and 60 of plate 56, openings 178 and 180 of spacer 170, openings 17 and 19 of stator assembly 12, openings 182 and 184 of spacer 172 and openings 3 and 5 of stator assembly 14 to secure those components to plate 56.

FIGS. 1 through 3 and 9 show the housing that contains the components of ultrasonic transducer 10. Housing 210 includes an upper housing member 211 and a lower housing member 144. The top of upper housing member 211 includes an opening 214 which contains a plate 215 formed from an acoustically-transparent material, such as vinyl. Plate 215 is a section of a sphere. The shape of plate 215 ensures that the ultrasonic waves passing through plate 215 from all directions are distorted, if at all, uniformly. Plate 215 rests on shoulders 216 in opening 214 of upper housing member 211. A gasket 220 is cemented to lower edge 221 of upper housing member 211 to provide a liquid-tight seal when upper housing member 211 is secured to lower housing member 144. Upper housing member 211 also includes openings 222 and 224 for receiving threaded screws 223 and 225 that join upper housing member 211 to lower housing member 144.

Upper housing member 211 includes a threaded opening 212 for receiving a filler plug 190. Filler plug 190 is a threaded plug having a shoulder 192 with a recess 194 into which an O-ring 196 is cemented. O-ring 196 ensures that the seal established between plug 190 and housing 210 is liquid tight. The other end of filler plug 90 includes a slot 200 for receiving the end of a rubber diaphragm 202. Rubber diaphragm 202 is held in place by a retaining ring 204 that fits over diaphragm 202 within slot 200 and establishes a liquid-tight seal therebetween. When the transducer 10 is cold, diaphragm 202 is under no pressure from within transducer 10. However, after transducer 10 becomes warm during its operation, acoustically-transparent liquid 15 expands at a rate that is highter than the rate at which upper housing member 211 expands. Accordingly, diaphragm 202 expands and prevents image deteriorating air bubbles from forming in transparent liquid 15.

Lower housing member 144 includes a base member 146 and a block member 147. Support plates 56 and 100 are secured within housing 210 to block 147. Eight screws 151 are threaded into openings 149 (only four shown) of block 147, through openings 106, 108, 110 and 112 of plate 100, and openings 107, 109, 111 and 113 of plate 56. Block 147 also includes an opening 117 into which a screw can be threaded through opening 115 of plate 56 to secure one end of a reed switch 52 to plate 56. Cable 156 passes through opening 158 of lower housing member 144 to permit electrical communication between the conductors of cable 156 and the components of transducer 10.

Transducer 10 includes switching devices for performing two functions. A first switching device provides information to transducer 10 that enables transducer 10 to energize only the transducer element 13 that is in a position to direct ultrasonic waves through plate 215. A second set of switching devices provides information to the scanning system from which it can synchronize image creation with transducer operation.

Plate 100 includes an opening 132 for receiving a commutating magnet 130. Commutating magnet 130 closes a reed switch 134, 136 or 138 secured at 120 degree intervals to magnet assembly 11 each time a reed switch 134, 136 or 138 comes within the magnetic field established by commutator magnet 130. When one of the reed switches 134, 136 or 138 closes, its corresponding transducer 13 is in a position to direct ultrasonic waves through cover 215 and that reed switch closes and enables the pulser circuit to send electrical pulses to that transducer 13. The pulser circuit (not shown) can be of any suitable configuration generally known.

A fourth reed switch 52 is secured within opening 54 formed in plate 56. Of the twenty-four magnet elements 32 in magnet assembly 11, three elements 33, disposed in magnet assembly 11 at 120 degree intervals and each disposed 180 degrees from its corresponding transducer element 13, are capable of activating reed switch 52 when reed switch 52 is disposed within the magnetic field generated by one of the elements 33. Accordingly, reed switch 52 provides information to the digital phase lock loop (hereinafter referred to as the "PLL circuit") from which that circuit produces image synchronization information in a form suitable for use by the scanning system. The PLL circuit is described in detail below.

Electrical signals are provided to components of transducer 10 and received by the scanning system therefrom via cable 156. Specifically, the scanning system provides signals to and receives signals from stator assemblies 12 and 14; reed switches 52, 134, 136 and 138; and transducer elements 13.

Transducers 13 receive pulsing signals from the pulsing circuit through reed switches 134, 136 and 138 and pass electrical signals related to ultrasonic echoes received by transducer elements 13 therethrough to a receiver circuit. Accordingly, a transducer element 13 can receive pulsing signals from the pulser circuit and transmit electrical signals to the receiver circuit only, when its corresponding reed switch 134, 136 or 138 is within the field created by commutating magnet 130. One side of each reed switch 134, 136 and 138 communicates with the pulser and receiver circuits through region 88 of plate 20. Regions 86, 88 and 90 are defined by insulating grooves 82 and 84 etched into the copper-plated surface 85 of plate 20. Cap 96, having a nipple 98, is soldered to region 88 and bears against carbon bearing 116 which is contained within metal container 118. An electrically conducting lead 140 from cable 156 passes through opening 114 of plate 100 and opening 120 of Teflon bushing 124 and is soldered to container 118 at point 122. Lead 140 electrically communicates with the pulser and receiver circuits of the scanning system. Lead 140 is shielded by shield 128 secured to plate 100. Accordingly, lead 140 provides pulsing signals to and receives electrical signals from transducer elements 13 through container 118, contact 116, cap 96, region 88 of plate 20, and reed switch 134, 136 or 138. The remaining connection of each reed switch 134, 136 and 138 is connected to the transducer element 13 corresponding thereto. Regions 86 and 90 are electrically grounded and provide the return path for the pulser and receiver circuits. The return connections of transducer elements 13 are soldered to region 86 of plate 20. A lead 92 connects electrically region 86 to region 90. One end of shaft 22 is soldered within opening 78 formed in region 90 of plate 20 and the remaining end of shaft 22 is in contact with contact 28 and, accordingly, plate 56, which is electrically grounded by a grounding conductor disposed in cable 156. Therefore, the return path for transducer elements 13 is region 86 of plate 20, conductor 92, region 90 of plate 20, shaft 22, contact 28, and plate 56.

Although it is preferable that the pulser and receiver circuits of the scanning system be disposed within housing 210, those circuits can be located in any suitable location. The pulser and receiver circuits can be of any known suitable configuration.

Energizing current for stator assemblies 12 and 14 can be provided directly from the motor control circuit, described in detail below, since stator assemblies 12 and 14 are stationary relative to transducer 10 during its operation.

Figure 11:
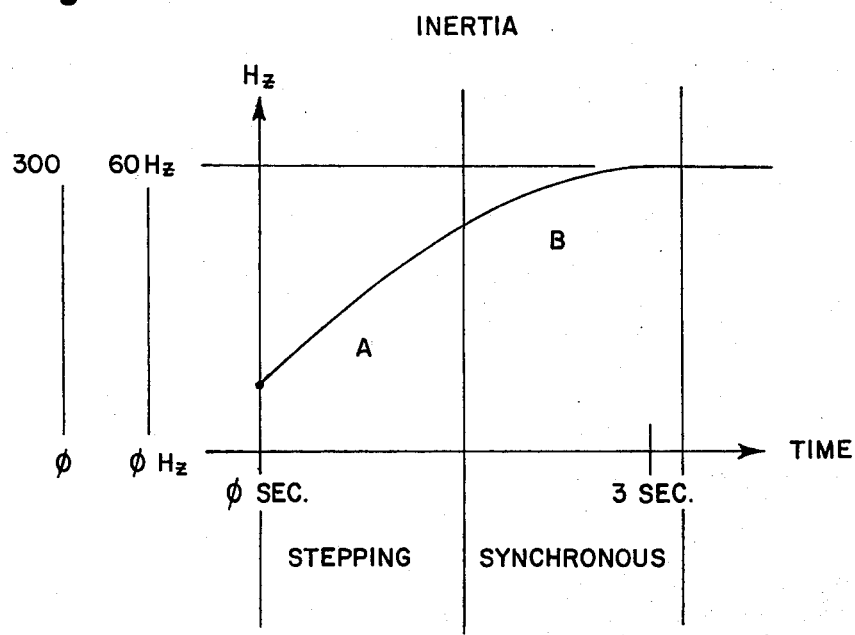
FIG. 11 is a graph of stator assembly energizing voltage frequency versus time.
Figure 10:
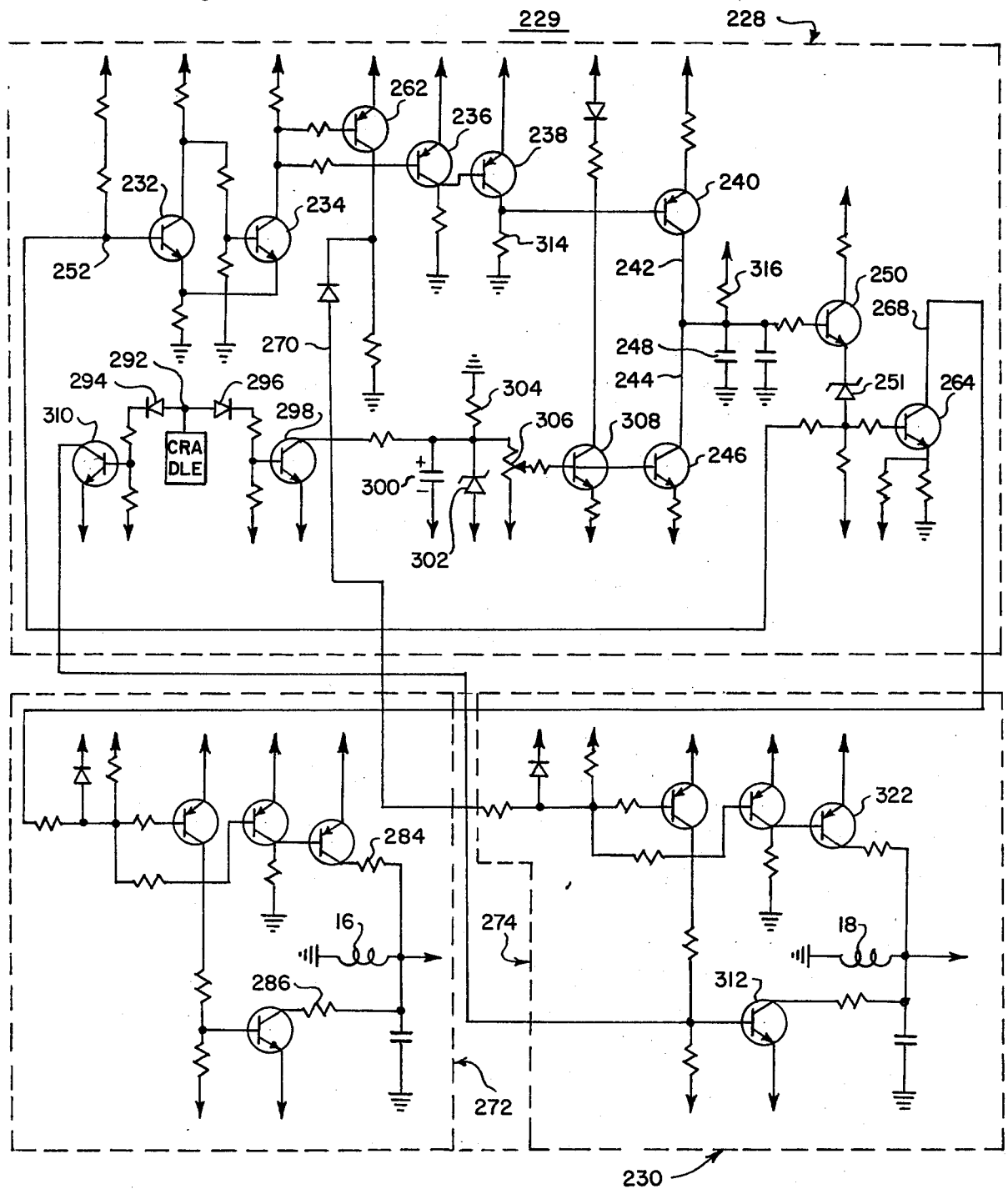
FIG. 10 is a circuit diagram of the motor control circuit for the ultrasonic transducer shown in FIG. 1.
Figure 12:
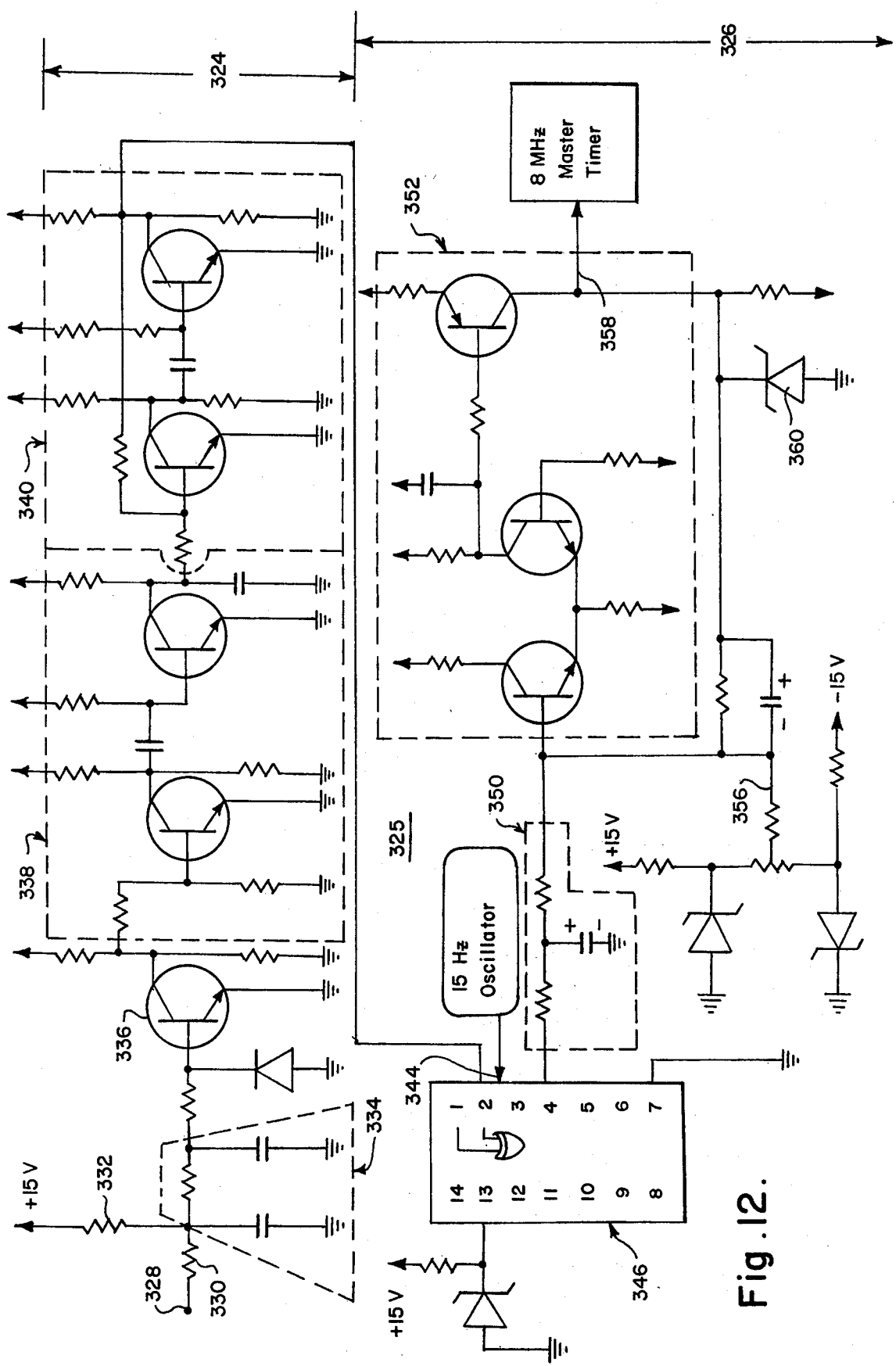
FIG. 12 is a circuit diagram of the phase lock loop circuit for the ultrasonic scanning transducer shown in FIG. 1.

FIG. 10 shows the motor control circuit 229 which produces the electrical signals that enable stator assemblies 12 and 14 to rotate magnet assembly 11. Circuit 229 includes circuit 228, which produces the control signals for application to stator assemblies 12 and 14, and circuit 230, which amplifies the signals created by circuit 228 and applies those amplified signals to stator assemblies 12 and 14. FIG. 11 shows a plot of the frequency of the periodic signal applied by circuit 229 to stator assemblies 12 and 14 versus time. When transducer 10 is first energized, at time zero, circuit 229 applies a 10 hertz periodic signal to stator assemblies 12 and 14. Circuit 229 gradually increases the frequency of the signal throughout the start-up phase until magnet assembly 11 achieves synchronous speed after approximately three seconds. During the start-up phase the apparatus functions like a stepping motor as magnet assembly 11 rotates in steps upon each reversal of the magnitude of the signal produced by circuit 229. As the frequency of the energizing signal increases, the angular velocity of magnet assembly 11 increases until, when it reaches synchronous speed, magnet assembly 11 rotates smoothly.

Transistors 232 and 234 form the heart of a Schmitt trigger, the output of which drives transistors 236 and 238. Transistors 240 and 246 are current sources which are controlled by the outputs of transistors 236 and 238. Transistors 236 and 238 and the Schmitt trigger coact to either produce a current that negates the output of current source 240 or allow it to produce its normal output. Current source 240 always produces current on line 242 that has a magnitude twice that of current source 246 produced on line 244. When current source 246 conducts, capacitor 248 uniformly discharges so that the voltage on it becomes negative. When transistors 236 and 238 are turned on, current source 240 uniformly recharges capacitor 248. Accordingly, at all times, capacitor 248 is either uniformly charging or discharging. Thus, the voltage across capacitor 248 is, during operation, a periodic signal.

Figure 7:
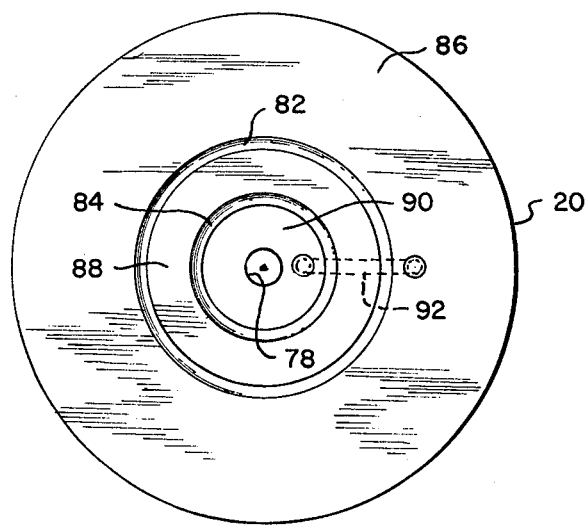
FIG. 7 is a front elevational view of the magnet end plate shown in FIG. 1.
Figure 8:
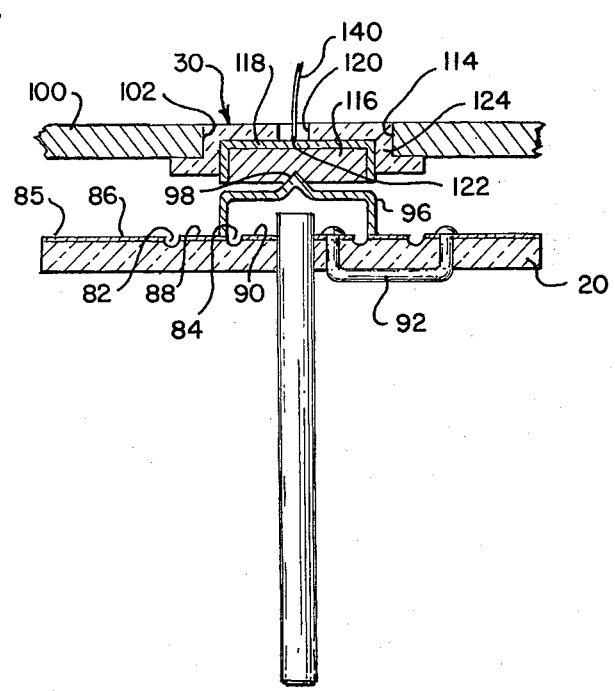
FIG. 8 is an enlarged view, partly in section, of the circular plate, shaft, and contact block shown in FIG. 1.

During normal operation of transducer 10, after the start-up phase indicated in FIG. 7, the voltage across capacitor 248 is amplified by transistor 250 and reflected back to point 252 by zener diode 251. The positive and negative peaks of the voltage across capacitor 248 control the switching of transistors 232 and 234 and enable the Schmitt trigger to produce a periodic signal of, preferably, 60 hertz. Transistors 262 and 264 converts the triangular waves produced by the Schmitt trigger and capacitor 248, respectively, to square waves at points 268 and 270.

The motor commands on points 268 and 270 are applied to amplifiers 272 and 274 of circuit 230. Circuits 272 and 274 are current switching amplifiers that apply the motor commands to coils 16 and 18 of stator assemblies 12 and 14, respectively. By selecting appropriate values of resistors 284 and 286 the current applied to coils 16 and 18 can be precisely controlled. It should be noted that it is possible to apply approximately sinusoidal waves to coils 16 and 18 by replacing switching amplifiers 272 and 274 with linear amplifiers. The 180 electrical degree separation of coils 16 and 18 ensures that the motor control circuit 229 can start rotation of magnet assembly 11 without regard to the orientation of magnet assembly 11 within housing 210.

While transducer 10 is resting in its cradle (not shown) prior to its start-up phase of operation, the cradle connection 292 short-circuits diodes 294 and 296 and turns on transistor 298. When transistor 298 is turned on, capacitor 300, connected across zener diode 302, discharges. When transducer 10 is lifted from its cradle, current driving transistor 298 is turned off, capacitor 300 is no longer short-circuited and it charges through resistor 304 until zener diode 302 clamps the voltage across capacitor 300 when it reaches a predetermined level, preferably five volts. Potentiometer 306 applies a portion of the voltage across capacitor 300 to the base of transistor 308 thereby causing transistors 308 and 246 to produce current. Accordingly, during start-up, the magnitude of the voltage applied to the base of transistor 246 gradually increases from zero to a predetermined maximum portion of the voltage across capacitor 300; that maximum voltage is always present on the base of transistor 246 during normal operation of the transducer 10. At all times, the current generated by transistor 240 is twice that generated by transistor 246. Therefore, since the rate at which capacitor 248 charges and discharges depends directly on the magnitude of the voltage applied to the base of transistor 246, the lower the base voltage of transistor 246, the lower the frequency of the output of circuit 228. The output of circuit 228 is, accordingly, a square wave having the same maximum amplitude during start-up and normal operation, but having time-varying frequency during the start-up phase and a constant frequency thereafter.

It should also be noted that circuit 229 applies a small bias voltage to one of the coils 16 or 18 of stator assemblies 12 or 14 when transducer 10 is not in operation and is resting in its cradle to limit the viscosity of acoustic fluid 13 and to maintain the temperature level of housing 210 at a minimum value. When transducer 10 is in its cradle, transistor 310 conducts current and short-circuits the driving current of transistor 312 and defeats the current in coil 18. Accordingly, amplifier 272 applies a voltage having a constant magnitude to coil 16 and amplifier 274 is prevented from applying a voltage to coil 18. The voltage applied to coil 16 produces the heat necessary to achieve the goals identified above.

It should be noted that resistor 314 causes the frequency of the triangular signal across capacitor 248 to increase smoothly during the start-up phase. Resistor 316 is necessary to give capacitor 248 a net positive residual current of approximately five percent of the normal operating current of transducer 10. That residual current is enough to ensure that when transducer 10 is in the cradle, current sources 308, 246 and 240 are turned off because capacitor 300 is discharged. Accordingly, the currents affecting capacitor 248 are only the currents flowing through resistor 316 and the normal base current of transistor 250. The current flowing through resistor 316 should always exceed the base current of transistor 240 at the lowest temperature of transistor 240 so that capacitor 248 always charges in the positive direction and ensures that only transistors 282 and 312 of amplifiers 272 and 274 can conduct and that transistors 280 and 322 will never conduct.

Figure 9:
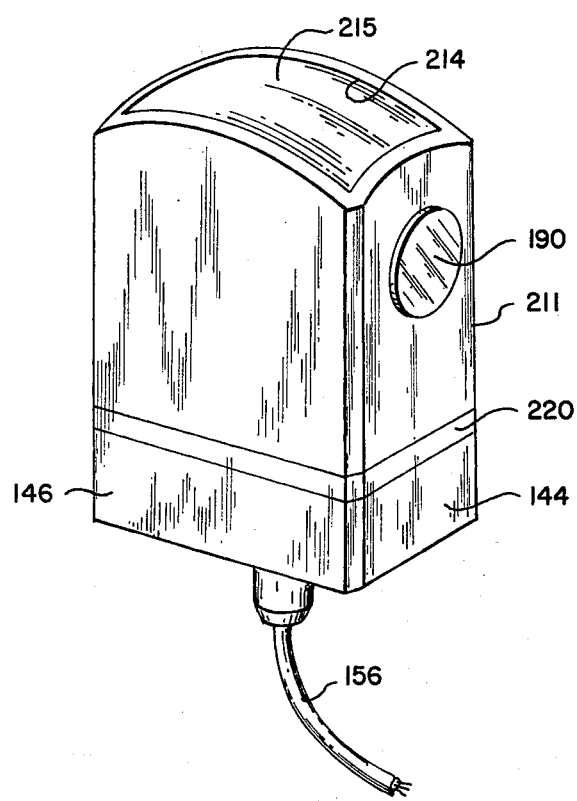
FIG. 9 is an isometric view of the housing for the ultrasonic scanning transducer shown in FIG. 1.

PLL circuit 325 is shown in FIG. 9. PLL circuit 325 ensures that the imaging circuitry of the scanner system produces frames of its display at the same rate that transducer 10 scans the object under examination. Circuit 324 of phase lock loop 325 converts the switching of commutator reed switch 52 to a square wave. Commutator reed switch 52 momentarily short-circuits the connection at 328 to ground through resistor 330, and causes the voltage across resistor 332 to be a square wave. Network 334 smooths the waveform across resistor 332 to permit only switch 52 to effect circuit 325 and thus prevent pulses from transducers 13 from causing transistor 336 to fire prematurely. Transistor 336 is a buffer transistor which operates pulse-forming network 338. Circuit 338 produces a short trigger pulse that activates one-shot multivibrator 340 which produces a 15 hertz square wave having a 50 percent duty cycle. The output of circuit 324 is applied to an exclusive OR gate 346, to which a 15 herz signal is also applied at point 344. The signal applied at point 344 is the output from the master timer of the scanning system and controls the rate at which frames of the display are produced by the imaging system. The output of gate 346 is that of the phase detector of a conventional phase lock loop circuit. Low pass filter 350 filters the output of OR gate 346. Operational amplifier 352 is constructed from discrete components to enhance its reliability and adds the output of filter 350 to a DC bias signal at 356. Operational amplifier 352 shifts the level of the output of filter 350 algebraically and provides an output signal at 358 which is clamped by zener diode 360 between levels of a negative one-half volt and a positive five volts. Circuit 326 compares the 15 hertz square wave formed by circuit 324—which is related to transducer motion—with the digital timing signal produced by the master timer of the scanning system. If those two signals are not in a quadrature phase relationship, circuit 326 provides an output that pulls the master timer into synchronization with the motion of magnet assembly 11.

Preferably, the components identified above by the following reference numerals should be of the type indicated below:

| Reference Numeral | Type |
|---|---|
| Resistors | |
| 284 | 10.0 ohms (5 watt) |
| 286 | 13.0 ohms (5 watt) |
| 304 | 6.8K ohms |
| 306 | 2.0K ohms |
| 314 | 390.0K ohms |
| 316 | 220.0K ohms |
| 330 | 1.0K ohms |
| 332 | 100.0K ohms |
| Diodes | |
| 251 | |
| 294 | 1N914 |
| 296 | 1N914 |
| 302 | |
| 360 | |
| Capacitors | |
| 248 | 1.0 microfarads (5%, 250 volt) |
| 300 | 220.0 microfarads (20%, 25 volt DC) |
| Transistors | |
| 232 | 2N3904 |
| 234 | 2N3904 |
| 236 | 2N3906 |
| 238 | 2N3906 |
| 240 | 2N3906 |
| 246 | 2N3904 |
| 250 | 2N3904 |
| 262 | 2N3906 |
| 264 | 2N3904 |
| 298 | 2N3904 |
| 308 | 2N3904 |
| 310 | 2N3904 |
| 312 | 2N3904 |
| 322 | 2N5192 |
| 336 | 2N5195 |
| Miscellaneous Components | |
| 346 | LS86 |

What is claimed is:

1. Ultrasonic scanning apparatus adapted for use in an ultrasonic scanning system that examines an object by directing a timed series of ultrasonic waves into the object and provides to the scanning system information carried by the returning ultrasonic echoes generated when the waves strike acoustical interfaces within the object comprising:
   a housing containing matter through which the ultrasonic waves and echoes can travel;
   means disposed within said housing for creating ultrasonic waves from electrical energy;
   means disposed within said housing for creating information carrying electrical energy from ultrasonic waves;
   a permanent magnet disposed within said housing and mounted therein for rotational movement for supporting at least one of said ultrasonic wave creating means and said electrical energy creating means;
   bearing means for mounting said permanent magnet for said rotational movement; and
   means secured within said housing for receiving a periodic electrical signal having a zero average value and creating, in response thereto, a unidirectionally rotating primary magnetic field capable of exerting a force on said permanent magnet and thereby rotating said permanent magnet in the direction of rotation of said primary magnetic field.

2. The ultrasonic scanning apparatus recited in claim 1 wherein said means for creating said primary magnetic field comprises a stator assembly secured to said housing including at least one electrical conductor forming at least one coil.

3. The ultrasonic scanning apparatus recited in claim 2 wherein said stator assembly includes at least two stator subassemblies.

4. The ultrasonic scanning apparatus recited in claim 3 wherein said stator assembly includes at least one said conductor on each said stator subassembly, each of said conductors forming at least one coil on each said stator subassembly.

5. The ultrasonic scanning apparatus recited in claim 2 wherein each said stator assembly is a laminate comprising at least two layers.

6. The ultrasonic scanning apparatus recited in claim 2 wherein said stator assembly includes slots for receiving said conductor.

7. The ultrasonic scanning apparatus recited in claim 2 wherein said conductor forms 24 coils.

8. The ultrasonic scanning apparatus recited in claim 2 wherein said stator assembly includes two conductors forming 24 coils.

9. The ultrasonic scanning apparatus recited in claim 1 wherein said means for creating ultrasonic waves and said means for creating electrical energy are at least one ultrasonic transducer element secured to said permanent magnet.

10. The ultrasonic scanning apparatus recited in claim 9 wherein three said transducer elements are secured to said permanent magnet.

11. The ultrasonic scanning transducer recited in claim 10 wherein said permanent magnet is cylindrical in shape and said transducer elements are secured to the outer surface of said permanent magnet at equal intervals around the perimeter of said permanent magnet.

12. The ultrasonic scanning apparatus recited in claim 1 wherein said permanent magnet is formed from at least two permanent magnet elements, said elements joined together to provide each element with a polarity opposite to that of its adjacent elements.

13. The ultrasonic scanning apparatus recited in claim 12 wherein the number of poles of said permanent magnet equals the number of said coils.

14. The ultrasonic scanning apparatus recited in claim 1 further comprising means for passing electrical energy to said ultrasonic wave generating means from the pulser circuit of said scanning system and to the receiver circuit of said scanning system from said electrical energy generating means only when said ultrasonic wave generating means and said electrical energy generating means are in a predetermined position relative to said housing.

15. The ultrasonic scanning apparatus recited in claim 14 wherein said passing means comprises:
a switch for passing said electrical energy when said ultrasonic wave creating means and said electrical energy generating means are in said predetermined position and for blocking said electrical energy therefrom at all other times during operation of said ultrasonic scanning apparatus.

16. The ultrasonic scanning apparatus recited in claim 15 wherein said switch is a reed switch.

17. The ultrasonic scanning apparatus recited in claim 1 further comprising means for generating said periodic signal.

18. The ultrasonic scanning apparatus recited in claim 17 wherein said means for generating said periodic signal comprises:
means for receiving electrical energy and creating therefrom said periodic signal, said periodic signal generating means increasing the frequency of said periodic signal from zero hertz to a predetermined maximum during a start-up phase of operation of said apparatus and maintaining the frequency of said periodic signal at said maximum frequency during operation of said apparatus subsequent to said start-up phase.

19. The ultrasonic scanning apparatus recited in claim 18 wherein said periodic signal generating means further comprises means for applying a pre-start electrical signal to said stator assembly to maintain the temperature of said ultrasonic scanning apparatus at a predetermined level when said ultrasonic scanning apparatus is not in use, said pre-start-up electrical signal being insufficient to cause said ultrasonic scanning apparatus to enter said start-up phase.

20. Ultrasonic scanning apparatus adapted for use in an ultrasonic scanning system that examines an object by directing a times series of ultrasonic waves into the object and provides said scanning system with information borne by the ultrasonic echoes generated when said waves strike acoustical interfaces within the object comprising:
a housing containing a liquid through which said waves and echoes can pass;
at least one transducer element disposed within said housing for receiving electrical energy and, in response thereto, directing ultrasonic waves into the object and for receiving the ultrasonic echoes and generating therefrom information-bearing electrical energy;
a permanent magnet to which said transducer element is fixed, said permanent magnet being mounted within said housing for rotational movement;
bearing means for mounting said permanent magnet within said housing for said rotational movement; and
a stator assembly for receiving a periodic electrical signal having a zero average value and, in response thereto, establishing a unidirectionally rotating primary magnetic field capable of exerting a force on said permanent magnet and rotating said permanent magnet and transducer element in the direction of rotation of said primary magnetic field.

21. The ultrasonic scanning apparatus recited in claim 20 wherein said stator assembly comprises:
at least one stator subassembly each having at least two magnetic stator plates joined together; and
at least one electrical conductor forming at least one coil on each said stator subassembly.

22. The ultrasonic scanning apparatus recited in claim 21 wherein said stator plates have slots formed in their perimeters to receive said electrical conductor.

23. The ultrasonic scanning apparatus recited in claim 22 wherein said conductor forms 24 coils.

24. The ultrasonic scanning apparatus recited in claim 22 wherein said stator assembly includes at least two stator subassemblies, said coil of each said stator subassembly being angularly shifted 90 electrical degrees from said coil of each adjacent stator subassembly.

25. The ultrasonic scanning apparatus recited in claim 24 wherein said permanent magnet is fabricated from at least two magnet elements.

26. The ultrasonic scanning apparatus recited in claim 25 wherein said magnet elements are joined together to provide each said magnet element with a polarity opposite to that of each magnet element adjacent to it.

27. The ultrasonic scanning apparatus recited in claim 26 wherein said permanent magnet includes 24 said magnet elements.

28. The ultrasonic scanning apparatus recited in claim 20 further comprising means for generating said periodic electrical signal.

29. The ultrasonic scanning apparatus recited in claim 28 wherein said periodic signal generating means comprises:
means for receiving electrical energy and creating therefrom said periodic electrical signal, said periodic signal generating means increasing the frequency of said periodic signal from zero hertz to a predetermined maximum during a start-up phase of the operation of said apparatus and maintaining the frequency of said periodic signal at said maximum during operation of said apparatus subsequent to said start-up phase.

30. The ultrasonic scanning apparatus recited in claim 29 wherein said periodic signal generating means further comprises means for applying a pre-start electrical signal to said stator assembly to maintain the temperature of said ultrasonic scanning apparatus at a predetermined level when said ultrasonic scanning apparatus is not in use, said pre-start electrical signal being insufficient to cause said ultrasonic scanning apparatus to enter said start-up phase of operation.

31. The ultrasonic scanning apparatus recited in claim 20 wherein said scanning system produces an image of a portion of the object and said ultrasonic scanning apparatus includes means for providing said scanning system with information from which said scanning system can synchronize the operation of the image production apparatus of the system with operation of said ultrasonic wave creating means and said ultrasonic echo receiving means.

* * * * *

UNITED STATES PATENT AND TRADEMARK OFFICE
CERTIFICATE OF CORRECTION

PATENT NO. :   4,398,425
DATED      :   August 16, 1983
INVENTOR(S) :  Terrance Matzuk It is certified that error appears in the above—identified patent and that said Letters Patent is hereby corrected as shown below:

Col. 1, line 20, delete "gather" and substitute therefor --gathers--.

Col. 4, line 34, delete "processional" and substitute therefor --precessional--.

Col. 5, line 17, delete "90" and substitute therefor --190--.

Col. 7, line 45, delete "verts" and substitute therefor --vert--.

Col. 11, line 51, delete "times" and substitute therefor --timed--.

Signed and Sealed this

Sixth Day of March 1984

[SEAL]

Attest:

Attesting Officer

GERALD J. MOSSINGHOFF

Commissioner of Patents and Trademarks